(12) United States Patent
Bahlmann et al.

(10) Patent No.: US 9,476,877 B2
(45) Date of Patent: Oct. 25, 2016

(54) **IN-VITRO PROCESS FOR THE QUICK DETERMINATION OF A PATIENT'S STATUS RELATING TO INFECTION WITH *MYCOBACTERIUM TUBERCULOSIS***

(71) Applicant: LOPHIUS BIOSCIENCES GMBH, Regensburg (DE)

(72) Inventors: Ferdinand Bahlmann, Saarbruecken (DE); Danilo Fliser, Heidelberg (DE); Martina Sester, Homburg (DE); Urban Sester, Homburg (DE)

(73) Assignee: LOPHIUS BIOSCIENCES GMBH, Regensburg (DE)

( * ) Notice: Subject to any disclaimer, the term of this patent is extended or adjusted under 35 U.S.C. 154(b) by 0 days.

(21) Appl. No.: 14/324,272

(22) Filed: Jul. 7, 2014

(65) Prior Publication Data

US 2015/0099652 A1 Apr. 9, 2015

Related U.S. Application Data

(63) Continuation of application No. 13/635,348, filed as application No. PCT/EP2011/054207 on Mar. 21, 2011, now abandoned.

(60) Provisional application No. 61/282,701, filed on Mar. 19, 2010.

(30) Foreign Application Priority Data

Mar. 19, 2010 (EP) ..................... 10157086

(51) Int. Cl.
| | | |
|---|---|---|
| *A61K 39/04* | (2006.01) | |
| *C12Q 1/00* | (2006.01) | |
| *A61K 39/02* | (2006.01) | |
| *G01N 33/569* | (2006.01) | |
| *G01N 33/68* | (2006.01) | |

(52) U.S. Cl.
CPC ...... *G01N 33/5695* (2013.01); *G01N 33/6863* (2013.01); *G01N 33/6866* (2013.01); *G01N 33/6869* (2013.01); *G01N 2333/55* (2013.01); *G01N 2333/57* (2013.01); *G01N 2800/56* (2013.01)

(58) Field of Classification Search
CPC .............................. A61K 39/00; A61K 39/04
USPC .............. 424/184.1, 234.1, 248.1; 435/4, 14, 435/40.5, 343.2
See application file for complete search history.

(56) References Cited

U.S. PATENT DOCUMENTS

2001/0006789 A1   7/2001   Maino

FOREIGN PATENT DOCUMENTS

| WO | 2008113119 | 9/2005 |
|---|---|---|
| WO | WO 2008/113119 | 9/2008 |

OTHER PUBLICATIONS

Dinser et al. "Evaluation of latent tuberculosis infectin in patients with inflammatory arthorpathies . . . " Rheumatology 2008; 47: 212-218.
Dirks et al, "Analysis of tuberculin-specific CD4 T-cell cytokine . . . " hand-out, congress of Neustadt, Germany (so called Saarlandisch Pfalzischer . . . ) Sep. 13-16, 2009.
Dirks et al. "Flow-cytometric analysis of antigen-specific CD4 T-cell cytokine . . . " hand-out; European congress of Immunology, Berlin, Germany, Mar. 7, 2009.
Sargentini et al. "Cytometric detection of antigen-specific IFN-β/IL-2 secreting cells in the diagnosis of tuberculosis" BMC Infections Diseases, vol. 9, 99, 2009, pp. 1-10.
Millington et al. "Dynamic Relationship between IFN-β and IL-2 Profile of *Mycobacterium*," The Journal of Immunology, vol. 178, No. 8, Apr. 14, 2007, pp. 5217-5226.
Sester et al. "Whole-blood flow-cytometric analysis of antigen-specific CD4 T-cell cytokine profiles distinguishes . . . " PLOS One, vol. 6, No. 3, Mar. 2011, E17813, p. 1-7.
Bal et al. "Dysregulation of proinflammatory and regulatory cytokines in HIV infected persons with active tuberculosis" Cytokine, vol. 30, 2005, pp. 375-281.
Valeria et al. "The level of PPD-specific IFN-β-producing CD4+ T cells in the blood predicts the in vivo response to PPD" Tuberculosis, vol. 87, 2007, 202-211.
Ranganathan et al. "Recombinant pro-apoptotic *Mycobacterium tuberculosis*.," Vaccine, vol. 28, 2010, pp. 152-161.
Bronke et al. "Direct Ex Vivo Detection of HLA-DR3-Restricted Cytomegalovirus . . . " Human Immunology, vol. 66, 2005, pp. 950-961.
Suni et al. "Detection of antigen-specific T cell cytokine expression in whole . . . " Journal of Immunological Methods, vol. 212, 1998, pp. 89-98.

(Continued)

*Primary Examiner* — Rodney P Swartz
(74) *Attorney, Agent, or Firm* — Jacobson Holman PLLC (57) ABSTRACT

An in-vitro process for the quick determination of the infection status of a *Mycobacterium tuberculosis* infection from whole blood in terms of active or latent tuberculosis, comprising the steps of:
  stimulating an antigen-specific T cell that is present in a first sample of whole blood with purified protein derivative (PPD) in the presence of antibodies against CD28, or CD28 and CD49d;
  processing of PPD by antigen-presenting cells (APC) by incubating for 1.5 h to 2.5 h, especially for 2 h, at 35° C. to 39° C., especially at 37° C., optionally with adding $CO_2$;
  then adding a secretion inhibitor;
  effecting an intensive mixing; and
  another incubation for a period of at least 2.5 h at a temperature of from 35° C. to 39° C., and
  determining a cytokine profile from both the intracellular INF-γ production and the intracellular IL-2 production of the antigen-specific T cell; wherein
  the presence of an active tuberculosis is indicated by a shift of the cytokine profile towards IFN-single positive cells accompanied by a decrease of IFN-γ/IL-2 double positive T cells.

19 Claims, 6 Drawing Sheets

(56) References Cited

OTHER PUBLICATIONS

Streitz et al. "Loss Receptor on Tuberculin-Reactive T-Cells Marks Active Pulmonary Tuberculous" PLOS One, Issue 8, E735, Aug. 2007, pp. 1-10.

Maecker et al. "Standardization of cytokine flow cytometry assays." BMC Immunology, vol. 6, No. 13, 2005, p. 1-18.

Meier et al. "Sensitivity of new commercial enzyme-linked immunospot assay . . . " Eur J Clin Microbiol Infect Dis, vol. 24, 2005, pp. 529-536.

Maino et al. "Identification of Functional Subsets by Flow Cytometry: Intracellular . . . " Cytometry, vol. 34, 1998, pp. 207-215.

Martins et al. "The level of PPD-specific IFN-gamma-producing CD4+ T cells in the blood predicts the in vivo response to PPD" Tuberculosis, vol. 87, No. 3, Apr. 11, 2007, pp. 202-211.

Winkler et al. "Increased specific T cell cytokine responses in patients with active pulmonary tuberculosis from Central Africa," Microbes and Infection, vol. 7, No. 9-10, Jul. 1, 2005.

Bronke et al. "Direct Ex Vivo Detection of HLA-DR3-Restricted Cytomegalovirus- and *Mycobacterium tuberculosis*-Specific CD4<+> T Cells." Human Immunology, vol. 66, No. 9, Sep. 1, 2005, pp. 950-961.

Ranganathan U D K et al. "Recombinant pro-apoptotic *Mycobacterium tuberculosis* generates CD8<+> T cell responses against human immunodeficiency virus type 1 Env and *M. tuberculosis* in neonatal mice." Vaccine, vol. 28, No. 1, Dec. 10, 2009, pp. 152-161.

Suni M A et al. "Detection of antigen-specific T cell cytokine expression in whole blood by flow cytometry." Journal of Immunological Methods, vol. 212, No. 1, Jan. 1, 1998, pp. 89-98.

Maino et al. "Identification of functional subsets by flow cytometry: Intracellular detectin of cytokine expression." Cytometry, vol. 34, No. 5, Oct. 15, 1998, pp. 207-215.

Maecker et al. "Standardizatin of cytokine flow cytometry assays." BMC Immunology, vol. 6, No. 1, Jun. 24, 2005, p. 13.

Meier et al. "Sensitivity of a new commercial enzyme-linked immhnospot assay (T SPOT-TB) for diagnosis of tuberculosis in clinical practice." European Journal of Clinical Microbiology & Infectious Disease, vol. 24, No. 8, Aug. 1, 2005, pp. 529-539.

Sester et al. Whole-blood flow-cytometric analysis of antigen specific CD4 T-cell cytokine profiles distinguishes active tuberculosis from non-active states. PLOS One, Mar. 15, 2011, vol. 6, issue 3, pp. 1-7.

Sester et al, "Flow-cytometric analysis of antigen-specific CD4 T-cell cytokine profiles distinguishes active tuberculosis from successfully treated disease." European Respiratory Society Annual Congress, Berlin 2008, Oct. 6, 2008, Clinical epidemlogy of tuberculosis, No. 1602.

Sargentini et al. Cytometric detection of antigen-specific IFN-y/IL-2 secreting cells in the diagnosis of tuberculosis. BMC Infectious Diseases, Jun. 23, 2009, vol. 9, No. 99, pp. 1-10.

Millington et al. Dynamic relationship between IFN-y and IL-2 profile of Mycobacterium tuberculosis-specific T cells and antigen lad. The Journal of Immunology, Apr. 15, 2007, No. 178, No. 8, pp. 5217-5226.

Martins et al. "The level of PPD-specific IFN-y-producing CD4+ T cells in the blood predicts the in vivo response to PPD." Tuberculosis, Oct. 17, 2006, vol. 87, issue 3, pp. 202-211.

IN-VITRO PROCESS FOR THE QUICK DETERMINATION OF A PATIENT'S STATUS RELATING TO INFECTION WITH *MYCOBACTERIUM TUBERCULOSIS*

This is a continuation of Ser. No. 13/635,348, now abandoned filed, Nov. 6, 2012, which is a 371 of PCT/EP11/054207, filed Mar. 21, 2011, which claims the benefit of U.S. Provisional Application No. 61/282,701, filed Mar. 19, 2010, and which has priority of EP 10157086.9 filed Mar. 19, 2010, the disclosures of which are incorporated herein by reference.

The present invention relates to in-vitro processes for the quick determination of the infection status of a *Mycobacterium tuberculosis* infection from whole blood.

Figure 1:
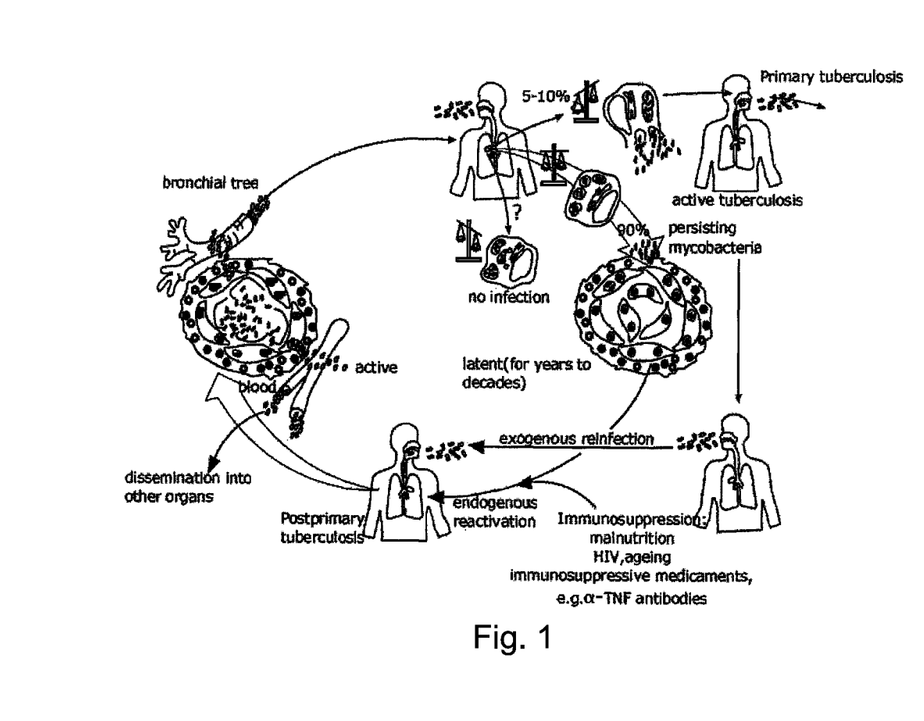
FIG. 1 depicts the infection cycle of *M. tuberculosis*.

Tuberculosis (TBC) is leading the worldwide statistics of deadly infectious diseases, wherein only about five to ten percent of those infected with *Mycobacterium tuberculosis* will become ill with tuberculosis in the course of their lives (FIG. 1). With the direct detection of the pathogen by laboratory diagnostics, the disease is clinically confirmed. By indirect detections with skin tests or an immunological test, the disease can only insufficiently be clinically diagnosed. Thus, it is currently not possible technically by means of the available diagnostic tests to get reliable information on a short-term basis, i.e., within a few hours, about the infection status of a patient suspected to be infected with tuberculosis.

The diagnosis of tuberculosis is ensured if a detection of the pathogens in culture is available. However, this is successful without difficulties only if the tuberculous tissue alterations are connected to the bronchial system, the efferent urinary tract or the intestine and can be excreted. Otherwise, it can be tried to obtain material by punctures with needles or directly by sampling tissue. Due to the slow growth of *Mycobacterium tuberculosis* on conventional solid media, in these cases, it is necessary to wait for four to six weeks to obtain a result, and in liquid cultures, the detection may be successful already after about two weeks with modern detection methods for mycobacterial growth.

In the indirect detection by means of a skin test or immunological detection, for example, in the Mendel-Mantoux intracutaneous tuberculin test, a defined amount of purified and filtered antigens from mycobacteria (tuberculin) is injected into the epidermis. If the immune system of the tested subject has had contact with mycobacteria before, a defense reaction with immigration of defense cells into the skin occurs at the respective site within three days, resulting in a swelling. This is a type IV reaction according to Coombs. As early as six weeks after an infection with TBC, the test may become positive. A palpable induration at the testing site is referred to as a positive reaction. This may mean that a tuberculosis infection has taken place. However, the test does not say anything about the presence of a disease. A positive test reaction is also possible after a tuberculosis vaccination. If the skin remains unchanged at the testing site or only shows a rash, this is considered a negative result. A tuberculosis infection is excluded then with a high probability.

To conclude, the intracutaneous tuberculin test is reliable only in a very limited way. On the one hand, it may remain negative just in severe courses, such as miliary tuberculosis or in immunosuppression, and on the other hand, earlier vaccination or contact with atypical mycobacteria leads to a false positive reaction.

As a further possible diagnostic method, immunological test methods, so-called interferon-gamma (IFN-γ) tests, have also been available since 2005. In this test, defense cells from the blood are stimulated with a mixture of antigens from *Mycobacterium tuberculosis*. If these cells have been in contact with the pathogens before due to a tuberculosis infection, they form an increased amount of the messenger IFN-γ. It can be determined in the cell supernatant, and in blood samples from infected subjects, it is at a clearly higher level than that of a negative control, which is to be carried along. For stimulation, the antigens ESAT-6 (early secreted antigenic target), CFP-10 (culture filtrate protein) and Tb7.7 are employed. They are formed in the early phase of infection and are not produced by most of the so-called non-tuberculosis mycobacteria, nor by the vaccination strains of the mycobacteria used for the BCG vaccination. This explains the very high specificity of the tests between true tuberculosis infections and infections from atypical mycobacteria or immunity acquired by vaccination. Two test systems for the IFN-γ test are currently approved in the European Union, namely QuantiFERON-TB® Gold In-Tube from Celiestis, which detects IFN-γ production by means of ELISA, and the T.SPOT.TB test from Oxford Immunotec, which also detects the number of producing T lymphocytes by means of Elispot in addition to the production of IFN-γ. In both tests, blood (QuantiFERON-TB® Gold In-Tube) or isolated mononuclear blood cells (T.SPOT.TB) must be incubated with the antigens for 20 hours, so that a test result is available on the next day at the earliest. The sensitivity of these tests for a past contact with *M. tuberculosis* is stated to range from 82 to 100% in different studies, the specificity in low-risk controls is being stated to be 98%. However, the performance of the tests is associated with difficulties and uncertainties in practice. The time window for the incubation and also the necessary constant temperature of 37° C. give rise to errors, as does the necessary experience with the method in the laboratory itself. Therefore, the stated values for the sensitivity and specificity are not reached by far in practice. As in all examination methods with sensitivities or specificities below 100%, its significance decreases with the prevalence rate of a true infection. Therefore, these in-vitro tests are not suitable for application in populations or occupational groups with a low prevalence either.

Marcia Valeria B. S. Martins et al. reported in Tuberculosis (2007) 87, 202-211 that the level of PPD-specific IFN-γ-producing CD4+ T cells in the blood predicts the in vivo response to PPD. Uma Devi Ranganathan et al. disclosed in Vaccine 28 (2010), 152-161 about recombinant pro-apoptotic *Mycobacterium tuberculosis* generating CD8+ T cell responses against HIV type 1 Env and *M. tuberculosis* in neonatal mice. Stefan Winkler et al. reported in Microbes and Infection 7 (2005) 1161-1169 about increased specific T cell cytokine responses in patients with active pulmonary tuberculosis from Central Africa. Corine Bronke et al published in Human immunology 66, 950-961 (2005) about direct Ex Vivo detection of HLA-DR3-restricted cytomegaiovirus- and *Mycobacterium tuberculosis*-specific CD4+ T cells. Vernon C. Maino and Louis Picker described intracellular detection of cytokine expression by flow cytometry (Cytometry 34:207-215 (1998). T. Meier et al reported in Eur J Clin Microbiol Infect Dis (2005) 24: 529-536 about sensitivity of a new commercial enzyme-linked immunospot assay (T SPOT-TB) for diagnosis of tuberculosis in clinical practice. Holden T. Maecker et al. reported in BMC Immunology 2005, 6:13 about standardization of cytokine flow cytometry assays. Maria A. Suni et al. disclose the detection of antigen-specific T cell cytokine expression in whole Blood by flow cytometry (Journal of Immunological Methods 212 (1998) 89-98). Streitz M, et al. reported that tuberculin-specific T-cell responses have low diagnostic specificity in BCG vaccinated populations. While subunit-antigen (e.g. ESAT-6, CFP-10) based tests are useful for diagnosing latent tuberculosis infection, there is no reliable immunological test for active pulmonary tuberculosis. Notably, all existing immunological tuberculosis-tests are based on T-cell response size, whereas the diagnostic potential of T-cell response quality has never been explored. This includes surface marker expression and functionality of mycobacterial antigen specific T-cells ((2007) Loss of Receptor on Tuberculin-Reactive T-Cells Marks Active Pulmonary Tuberculosis. PLoS ONE 2(8): e735 doi:10.1371/journal.pone.0000735).

WO-A-2008113119 discloses methods and kits for measuring a cell-mediated immune (CMI) in a small volume of whole undiluted blood collected from a subject. In particular, the methods are for measuring responses in undiluted whole blood samples having a volume of, for example, 50 µl to 500 µl. Thus, capillary sampling and rapid testing of subjects including pediatric, adult or geriatric human subjects are facilitated.

US-A-2001/0006789 discloses a novel approach to the assessment of antigen-specific T cells that quantities and characterizes these cells with unprecedented clarity, and importantly because it is performed in whole blood, is amenable to routine use in the clinical immunology laboratory. The methodology offers an improved cytometric intracellular cytokine assay in whole blood that can simultaneously measure multiple T cell subsets expressing multiple cytokines from a single whole blood culture. Evaluation of whole blood antigen specific cytokine responses has the important advantage of assessing T cell activation in the presence of ALL types of MHC autologous antigen presenting cells present in the native sample. It also has the advantage of enabling a culture system (whole blood) which can reflect effects of systemic environments (i.e. drug augmentation or suppression) on T cell responses to specific stimuli including antigen, by either culturing in the presence of such drug or analyzing the blood of a human or animal receiving such drug.

It is an object of the present invention to provide a process that avoids the drawbacks of the prior art and offers a quick and reliable diagnostic method that additionally allows distinguishing between an acute infection and a latent infection.

This object is achieved by an in-vitro process for the quick determination of the infection status of a *Mycobacterium tuberculosis* infection from whole blood in terms of active or latent tuberculosis, comprising the steps of:

stimulating an antigen-specific T cell that is present in a first sample of whole blood with purified protein derivative (PPD) in the presence of antibodies against CD28, or CD28 and CD49d;

processing of PPD by antigen-presenting cells (APC) by incubating for 1.5 h to 2.5 h, especially for 2 h, at 35° C. to 39° C., especially at 37° C., optionally with adding $CO_2$;

then adding a secretion inhibitor;

effecting an intensive mixing; and another incubation for a period of at least 2.5 h at a temperature of from 35° C. to 39° C., and determining a cytokine profile from both the intracellular INF-γ production and the intracellular IL-2 production of the antigen-specific T cell; wherein the presence of an active tuberculosis is indicated by a shift of the cytokine profile towards IFN-γ single positive cells accompanied by a decrease of IFN-γ/IL-2 double positive T cells.

In one embodiment of the process according to the invention, another stimula-tion with PBS, *Staphylococcus aureus* enterotoxin B superantigen (SEB), ESAT-6 CFP-10 and/or vaccination antigen may be effected in addition to said stimulation with PPD. This may be indicated when antigen-specific cells are present in order to decide whether these are due to contact with *Mycobacterium tuberculosis* or due to contact with non-tuberculous mycobacteria or due to a vaccination response.

In another embodiment of the invention, a negative control is performed by adding a buffer, in particular a physiologically acceptable buffer, such as PBS 0.9% NaCl or 5% Glucose to an antigen-specific cell that is present in the whole blood of a second sample, which is authentic with said first sample ("authentic with" meaning "derived from the same source as").

In another embodiment of the invention, a positive control can be performed by adding SEB to an antigen-specific T cell that is present in the whole blood of a third sample, which is authentic with said first sample.

In one embodiment, a vaccination control, in particular a BCG-vaccination control, can be effected by adding ESAT-6 (early secreted antigenic target) and CFP-10 (culture filtrate protein) to an antigen-specific T cell that is present in the whole blood of a fourth sample, which is authentic with said first sample. Alternatively, a control whether or not a contact with non-tuberculosis mycobacteria took place in the whole blood donor can be effected by adding ESAT-6 (early secreted antigenic target) and CFP-10 (culture filtrate protein) to an antigen-specific T cell that is present in the whole blood of a fourth sample, which is authentic with said first sample.

In another embodiment a vaccination control can take place by adding the vaccination antigen to an antigen-specific T-cell that is present in the whole blood of a fifth sample which is authentic with said first sample.

In still another embodiment of the process according to the invention, the secretion inhibitor is selected from the group consisting of brefeldin A, monensin or the like.

According to the invention, the determination of the cytokine profile is effected by means of suitable methods, such as flow cytometry.

The process according to the invention can be applied to whole blood samples from humans or animals.

The process according to the invention is particularly applied for contact tracing wherein whole blood was obtained from a person with close contact to a patient with active TB or suspect to have had a close contact to a patient with active TB. Furthermore, depending on the result of the diagnostic assay of the invention a treatment decision or regime is established as follows:

a. a prophylaxis, such as INH or an active treatment, such as quadruple therapy is indicated in cases, where a shift of the cytokine profile towards IFN-γ single positive cells accompanied by a decrease of IFN-γ/IL-2 double positive cells was detected;

b1. if diagnostic investigations revealed a latent infection with *Mycobacterium tuberculosis* by IFN-γ/IL-2 double positive cells and no information about previous testing is available, no acute therapy is necessary and the patient has to be retested within 2 to 4 weeks;

b2. if diagnostic investigations revealed a latent infection with *Mycobacterium tuberculosis* by IFN-γ/IL-2 double positive cells and if in previous testing for latent infection with *Mycobacterium tuberculosis* did reveal no contact with *Mycobacterium tuberculosis* so far, a prophylaxis, such as INH therapy is indicated;
c1. no acute therapy is indicated if the patient shows no response.
c2. in case the patient reveals any clinical symptoms, retesting is indicated.

The process according to the invention can further be employed to investigate whole blood which was obtained from a person before receiving immunosuppressive drugs or in an immune-incompetent state like HIV infection.

Depending on the result of the diagnostic assay of the invention a treatment decision or regime is established as follows:
a. a prophylaxis, such as INH or an active treatment, such as quadruple therapy, and optionally delaying of immunosuppressive therapy, is indicated in cases, where a shift of the cytokine profile towards IFN-γ single positive cells accompanied by a decrease of IFN-γ/IL-2 double positive cells was detected;
b1. if diagnostic investigations revealed a latent infection with *Mycobacterium tuberculosis* by IFNγ/IL-2 double positive cells and no information about previous testing is available, immunosuppressive therapy is possible and the patient has to be retested within 2 to 4 weeks;
b2. if diagnostic investigations revealed a latent infection with *Mycobacterium tuberculosis* by IFN-γ/IL-2 double positive cells and if in previous testing for latent infection with *Mycobacterium tuberculosis* did reveal no contact with *Mycobacterium tuberculosis* so far, a prophylaxis, such as INH therapy, and optionally delaying of immunosuppressive therapy, is indicated as well as retesting of the patient within 2 to 4 weeks;
c1. immunosuppressive therapy is to begin if the patient shows no response;
c2. in case the patient reveals any clinical symptoms, retesting is indicated.

The process according to the invention can further be employed to investigate whole blood which was obtained from a person suspected for an active TB infection.

Depending on the result of the diagnostic assay of the invention a treatment decision or regime is established as follows:
a. an active treatment, such as a quadruple therapy is indicated in cases, where a shift of the cytokine profile towards IFN-γ single positive cells accompanied by a decrease of IFN-γ/IL-2 double positive cells was detected;
b1. if diagnostic investigations revealed an latent infection with *Mycobacterium tuberculosis* by IFN-γ/IL-2 double positive cells and no information about previous testing is available, an acute infection is unlikely, an alternative diagnosis is to be considered, and the patient has to retested within 2 to 4 weeks;
b2. if diagnostic investigations revealed a latent infection with *Mycobacterium tuberculosis* by IFN-γ/IL-2 double positive cells and if in previous testing for latent infection with *Mycobacterium tuberculosis* did reveal no contact with *Mycobacterium tuberculosis* so far, a prophylaxis, such as INH or an active treatment, such as quadruple therapy is indicated and the patient has to be retested within 2 to 4 weeks;
c1. no acute therapy is indicated if the patient shows no response;
c2. in case the patient reveals any clinical symptoms, retesting is indicated.

The invention is further explained by means of the following Examples.

Figure 2:
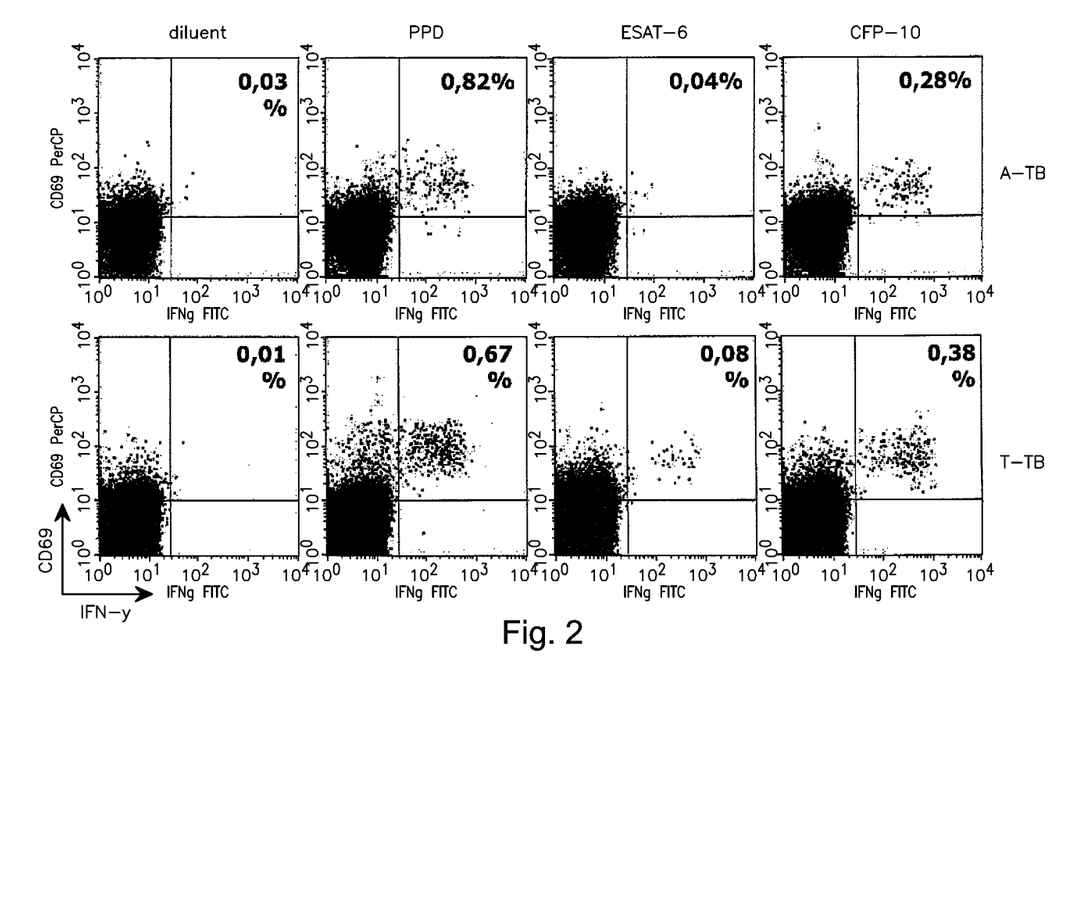
FIG. 2 shows a flow-cytometric analysis of the antigen-specific T cells, which were identified merely by the analysis of the cytokine IFN-γ. It was found that a distinction between an active tuberculosis (A-TB) and a successfully treated tuberculosis (T-TB) is not possible by the sole analysis of IFN-γ independently of the stimulation with PPD, ESAT-6 or CFP-10. ESAT-6 and CFP-10 only allow for a discrimination between patients having had contact with *M. tuberculosis* (ESAT-6 and/or CFP-10 positive) and patients with a pure BCG vaccination response (ESAT-6 and CFP-10 negative, not shown).
Figure 3:
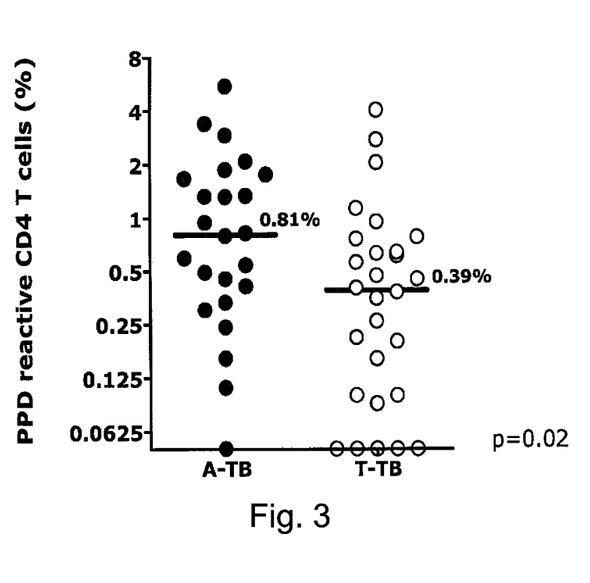
FIG. 3 shows the frequency distribution of PPD-specific T cells in patients with active tuberculosis (A-TB) and subjects with successfully treated tuberculosis (T-TB). The T cells were identified by the activation via CD69 and the specific induction of IFN-γ by PPD. It is found that although patients with A-TB have significantly higher frequencies of PPD-specific T cells, a distinction between an active tuberculosis (A-TB) and a successfully treated tuberculosis (T-TB) is not possible by the sole analysis of IFN-γ in the individual case due to the large overlap.
Figure 4:
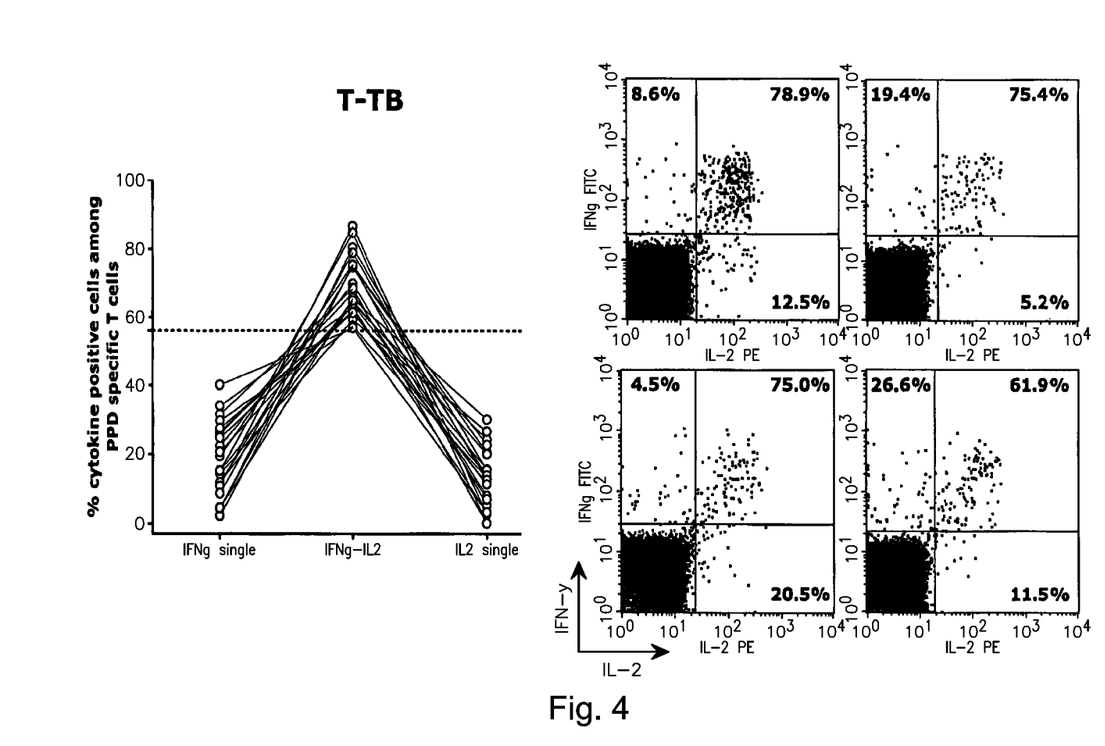
FIG. 4 exemplarily shows IFN-γ/IL-2 cytokine profiles of PPD-reactive T cells in four patients with successfully treated tuberculosis. The percentages of IFN-γ single positive, IFN-γ/IL-2 double positive and IL-2 single positive T cells is quantified in the Figure on the left side. The predominant proportion of the cells expresses both cytokines.
Figure 5:
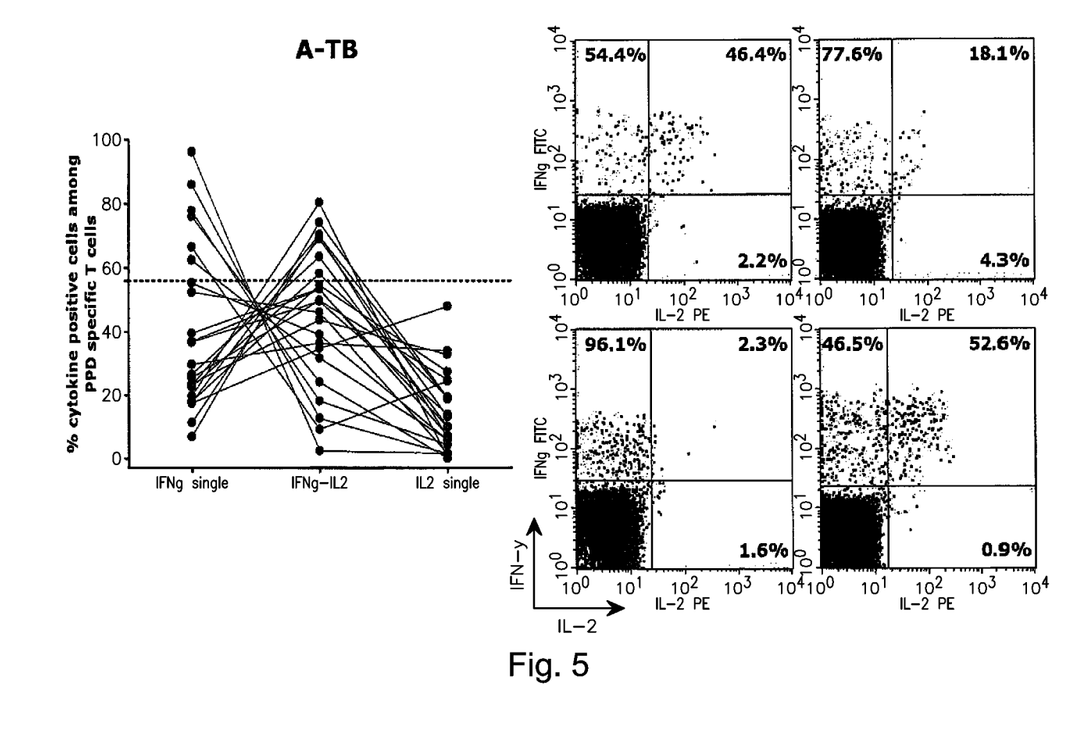
FIG. 5 exemplarily shows IFN-γ/IL-2 cytokine profiles of PPD-reactive T cells in four patients with active tuberculosis. The percentages of IFN-γ single positive, IFN-γ/IL-2 double positive and IL-2 single positive T cells is quantified in the Figure on the right-hand side. Patients with active tuberculosis exhibit a shift in the cytokine profile towards IFN-γ single positive cells accompanied by a decrease of IFN-γ/IL-2 double positive T cells.
Figure 6:
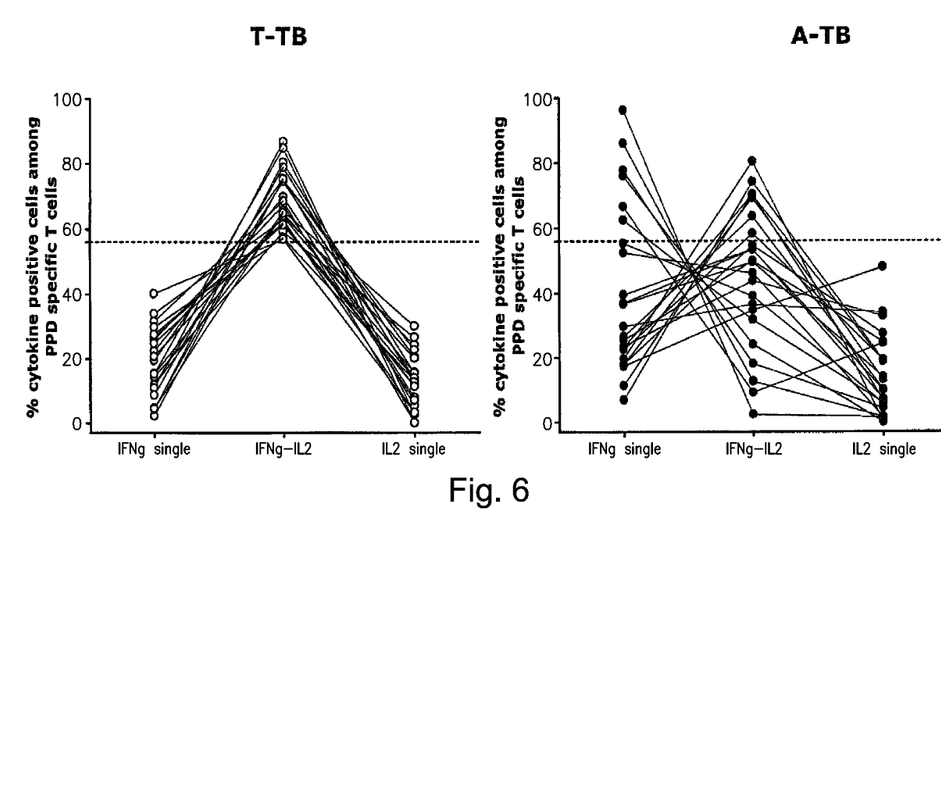
FIG. 6 shows a summarized representation of the cytokine profiles in patients with active tuberculosis (A-TB) and successfully treated tuberculosis (T-TB). The dashed line represents the limit of IFN-γ/IL-2 double positive T cells (56%) below which an active tuberculosis can be diagnosed with a specificity of 100% and a sensitivity of 70%. This limit was established by means of receiver operating characteristic (ROC) analysis.

Advantageously, the INF-γ production of the antigen-specific cell is determined intracellularly in the process according to the invention. Thus, the stimulation time of the antigen-specific T cells with the tuberculosis antigens PPD (purified protein derivative), ESAT-6 (early secreted antigenic target) and CFP-10 (culture filtrate protein) can be shortened to 6 hours in contrast to the 20 hours of the previous tests (FIG. 2). Although the determination of INF-γ expressing PPD-reactive T cells already occurs at a statistically significant higher frequency in patients with active tuberculosis as compared to patients with latent or successfully treated tuberculosis, a distinction between the two stages of the disease cannot be made for the individual patient due to a very large overlap range (FIG. 3). ESAT-6 and CFP-10 merely allow for the discrimination between patients having had contact with *M. tuberculosis* (ESAT-6 or CFP-10 positive) and patients with a pure BCG vaccination response (ESAT-6 and CFP-10 negative, not shown). However, the distinction between active and latent or successfully treated tuberculosis is enabled through the activation via CD69 in PPD-specific T cells and by the simultaneous determination of IFN-γ and interleukin-2 (IL-2). While the predominant fraction of the PPD-reactive T cells express both INF-γ and IL-2 in latent or successfully treated tuberculosis (FIG. 4), the cytokine profile will shift towards IFN-γ single positive cells in active tuberculosis (FIG. 5). By means of receiver operating characteristic (ROC) analysis, the limit of IFN-γ/IL-2 double positive PPD-reactive T cells below which an active tuberculosis can be diagnosed with a specificity of 100% is established. In the population present here, this limit is 56% of IFN-γ/IL-2 double positive T cells, patients with active tuberculosis (A-TB) can be distinguished thereby from patients with successfully treated tuberculosis (T-TB) with a sensitivity of 70% (FIG. 6).

In another embodiment, the determination of the cytokine profile is effected by means of flow cytometry with labeled antibodies. Thus, in addition to the determination of INF-γ, the simultaneous quantification of further functionally relevant surface molecules, such as PD-1 (programmed death-1), CTLA-4 (cytotoxic T-lymphocyte antigen 4), TIM-3 (T-cell immunoglobulin domain and mucin domain 3), or further cytokines, such as interleukin-2, TNF-α (tumor necrosis factor α) or IP-10 (chemokine (C-X-C motif) ligand 10) is also possible.

For the analysis of antigen-specific CD4 T cells by means of flow cytometry, specific T cells are excited by antigen stimulation to activation and cytokine production, and the number of excited cells is subsequently detected by means of specific antibodies. For the examination of *Mycobacterium tuberculosis* (MTB) specific T cells, the antigens PPD, ESAT-6 and CFP-10 are employed. For the distinction of active from latent/successfully treated tuberculosis, a test with PPD is performed, and for the differentiation of a latent/successfully treated tuberculosis infection from a previous vaccination, a test with ESAT-6 and CFP-10 is performed. PBS serves as a negative control, by which background signals, such as non-specifically responding T cells, can be established, SEB serves as a positive control.

The stimulation can be performed directly from whole blood. At first, the whole blood is mixed with CD28- and CD49d-specific antibodies at a concentration of 1 µg/ml each and admixed with the respective antigens (PPD: 7.32 µg/ml, tuberculin RT-50; Statens Serum institute, Copenhagen, Denmark), Stimulations were performed with Mtb-derived peptide pools covering ESAT-6 and CFP-10. CFP-10 and ESAT-6 peptides pools are composed of 15-mers overlapping by 11 amino acids, and all peptides were HPLC purified [>80% purity, Hariri et al. *Nature Medicine* 2011; 17: 372-376].

After 2 hours of incubation time (37° C., 6% $CO_2$), the exocytosis of the cytokines induced by the stimulation is stopped by the addition of 10 µg/ml brefeldin A (BFA) in order to accumulate the cytokines intracellularly. This is followed by another 4 hours of incubation (37° C., 6% $CO_2$).

The stimulation is interrupted after 6 hours, and the cells are fixed. At first, 2 mM EDTA is added to each sample, followed by mixing for 10 seconds and incubating at room temperature for 15 minutes. The fixation of the white blood cells and lysis of the erythrocytes is effected with 9 ml of Becton Dickinson lysing solution per milliliter of whole blood for an incubation time of 10 minutes at room temperature. After centrifugation and suction of the supernatant, the cell pellet obtained is washed with 2 ml of FACS buffer (PBS-5 FCS-0.5% BSA-0.0796 $NaN_3$). This is effected by adding the FACS buffer, followed by centrifuging and suction of the supernatant. Finally, the fixed cells are taken up in FACS buffer. The cells can now be stained directly or stored in the refrigerator at 4° C. over night. To stain the stimulated cells with specific fluorochrome-labeled antibodies, the cells are redistributed to FACS tubes. Leucocytes from about 225-300 µl of whole blood are used per staining mixture. At first, 2 ml of saponin buffer (FACS buffer/0.1% saponin) is added per sample for 10 min. After centrifugation and suction of the SAP buffer, the addition of the antibody mixture is effected in a total volume of 50 µl each per sample of FACS buffer/0.196 saponin (anti-CD4 clone SK3, anti-IFN-γ clone 4S.B3, anti-IL-2 clone MQ1-17H12, and anti-CD69 clone L78). Since the antibodies are light-sensitive, the 30 min incubation is effected in the dark at room temperature. Subsequently, the cells are washed with 3 ml of FACS buffer to remove unbound antibodies. Finally, the cell pellet is taken up in 150 µl of 1% paraformaldehyde solution and analyzed by means of flow cytometry.

In successfully treated tuberculosis, it is found that a predominant fraction of antigen-specific T cells express both IFN-γ and IL-2 upon specific stimulation with PPD. Surprisingly, when an active tuberculosis exists, the cytokine profile will shift towards IFN-γ single positive cells accompanied by a simultaneous decrease of IFN-γ/IL-2 double positive T cells. A latent or successfully treated tuberculosis infection can be distinguished from a vaccination response by stimulation with ESAT-6 and CFP-10. ESAT-6 and CFP-10 allow discriminating between patients having had contact with *M. tuberculosis* (ESAT-6 and/or CFP-10 positive) and patients with a pure BCG vaccination response (ESAT-6 and CFP-10 negative).

The invention claimed is:

1. An in-vitro process for the quick determination of the infection status of a *Mycobacterium tuberculosis* infection from whole blood in terms of an active or latent tuberculosis, comprising the steps of:
    stimulating an antigen-specific T cell that is present in a first sample of whole blood with purified protein derivative (PPD) in the presence of antibodies against CD28, or CD28 and CD49d;
    processing of PPD by antigen-presenting cells (APC) by incubating for 1.5 h to 2.5 h at 35° C. to 39° C. optionally with adding $CO_2$;
    then adding a secretion inhibitor;
    effecting a mixing; and
    another incubation for a period of at least 2.5 h at a temperature of from 35° C. to 39° C., and determining a cytokine profile from both the intracellular INF-γ production and the intracellular IL-2 production of the antigen-specific T cell;
    determining a baseline T cell profile from which a shift and decrease is determined by a receiver operating characteristic (ROC) analysis
wherein
    the presence of an active tuberculosis is indicated by frequencies of PPD-specific IFN-γ/IL-2 double positive T cells below 56%.

2. The process according to claim 1, wherein another stimulation with SEB, ESAT-6 and CFP-10 and/or *M. tuberculosis* vaccination antigen is effected in addition to said stimulation with PPD.

3. The process according to claim 1, wherein a negative control is performed by adding a physiological buffer such as PBS 0.9% NaCl or 5% Glucose to an antigen-specific T cell that is present in the whole blood of a second sample, which is identical with said first sample.

4. The process according to claim 1, wherein a positive control is performed by adding SEB to an antigen-specific T cell that is present in the whole blood of a third sample, which is identical with said first sample.

5. The process according to claim 1 wherein a vaccination control took place by adding the *M. tuberculosis* vaccination antigen to an antigen-specific T-cell that is present in the whole blood of a fourth sample which is identical with said first sample.

6. The process according to claim 1, wherein a BCG-vaccination control is effected by adding ESAT-6 (early secreted antigenic target) and CFP-10 (culture filtrate protein) to an antigen-specific T cell that is present in the whole blood of a fourth sample, which is identical with said first sample.

7. The process according to claim 1 wherein a control whether or not a contact with non-tuberculosis mycobacteria took place in the whole blood donor is effected by adding ESAT-6 (early secreted antigenic target) and CFP-10 (culture filtrate protein) to an antigen-specific T cell that is present in the whole blood of a fifth sample, which is identical with said first sample.

8. The process according to claim 1, wherein said secretion inhibitor is selected from the group consisting of brefeldin A and monensin.

9. The process according to claim 1, wherein the determination of the cytokine profile is effected by flow cytometry.

10. The process according to claim 3, wherein the whole blood of the samples is obtained from humans.

11. The process according to claim 1 further comprising obtaining whole blood from a person having contacted or suspected of having contacted a patient with active TB and testing the whole blood to determine contact tracing of the person.

12. The process according to claim 11 further comprising treating the person tested by INH prophylaxis or quadruple therapy when a shift of the cytokine profile towards IFN-γ single positive cells accompanied by a decrease of IFN-γ/IL-2 double positive cells is detected.

13. The process according to claim 1 wherein whole blood was obtained from a person before receiving immunosuppressive drugs or in an immune-incompetent state.

14. The process of claim 13 further comprising treating the person tested by INH prophylaxis or quadruple therapy when a shift of the cytokine profile towards IFN-γ single positive cells accompanied by a decrease of IFN-γ/IL-2 double positive cells is detected.

15. The process according to claim 1, wherein whole blood was obtained from a person suspected for an active TB infection.

16. The process of claim 15 further comprising treating the person tested by INH prophylaxis or quadruple therapy when a shift of the cytokine profile towards IFN-γ single positive cells accompanied by a decrease of IFN-γ/IL-2 double positive cells is detected.

17. The process according to claim 1, wherein processing of PPD by antigen-presenting cells (APC) is by incubating for 2 h at 37° C., optionally with adding $CO_2$.

18. The process according to claim 1, wherein a negative control is performed by adding a physiological buffer selected from the group consisting of PBS 0.9% NaCl and 5% Glucose to an antigen-specific T cell that is present in the whole blood of a second sample, which is identical with said first sample.

19. The process according to claim 3, wherein the whole blood of the samples is obtained from animals.

* * * * *